United States Patent
Nishiwaki et al.

(10) Patent No.: US 7,005,530 B2
(45) Date of Patent: Feb. 28, 2006

(54) PURIFICATION OF METAL HYDROCARBON

(75) Inventors: Hiromi Nishiwaki, Niigata-ken (JP);
Takanobu Tsudera, Niigata-ken (JP);
Takayuki Honma, Niigata-ken (JP);
Shuji Tanaka, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 239 days.

(21) Appl. No.: 10/868,980

(22) Filed: Jun. 17, 2004

(65) Prior Publication Data

US 2005/0004383 A1 Jan. 6, 2005

(30) Foreign Application Priority Data

Jun. 19, 2003 (JP) .................................... 2003-174387

(51) Int. Cl.
*C07F 5/00* (2006.01)

(52) U.S. Cl. ............................................................ 556/1
(58) Field of Classification Search ..................... 556/1
See application file for complete search history.

(56) References Cited

U.S. PATENT DOCUMENTS

| | | | |
|---|---|---|---|
| 4,720,561 A | | 1/1988 | Bradley et al. ................. 556/1 |
| 5,288,885 A | * | 2/1994 | Smit et al. ...................... 556/1 |

FOREIGN PATENT DOCUMENTS

| | | |
|---|---|---|
| JP | 62-185090 A | 8/1987 |
| JP | 5-35154 B2 | 5/1993 |
| WO | 85/04405 A1 | 10/1985 |
| WO | WO 93/10125 A1 | 5/1993 |

* cited by examiner

*Primary Examiner*—Porfirio Nazario-Gonzalez
(74) *Attorney, Agent, or Firm*—Birch, Stewart, Kolasch & Birch, LLP

(57) ABSTRACT

A contaminated Group III metal hydrocarbon is purified by providing an adduct of Group III metal hydrocarbon with a Lewis base in a solvent having a boiling point which is up to 200° C., but at least 30° C. higher than the boiling point of the Group III metal hydrocarbon, separating the solvent from the adduct, and heating the adduct for thermal dissociation, thereby releasing the Group III metal hydrocarbon in high purity form.

8 Claims, No Drawings

PURIFICATION OF METAL HYDROCARBON

This Nonprovisional application claims priority under 35 U.S.C. §119(a) on Patent Application No. 2003-174387 filed in JAPAN on Jun. 19, 2003, the entire contents of which are hereby incorporated by reference.

TECHNICAL FIELD

This invention relates to a method for purifying a metal hydrocarbon which is useful in the manufacturing of compound semiconductor materials.

BACKGROUND ART

The outstanding development of fast personal communications like mobile phones has posed an increasing demand for semiconductor devices using Group III compound semiconductor materials such as gallium arsenide and gallium nitride. Also, compound semiconductor diodes have reached the practical utilization level and are expected to have an increasing demand because of their high emission efficiency.

These materials are generally manufactured by the vapor phase growth of organometallic compounds using reactants in the form of Group III metal alkyls having alkyl groups as a constituent component, such as trimethyl gallium, trimethyl aluminum, trimethyl indium and triethyl gallium.

The characteristics of a compound semiconductor are largely affected by the purity of a Group III metal alkyl as the starting reactant. Even traces of impurities can noticeably detract from optical and electrical characteristics. It would be desirable to have a method for preparing high purity Group III metal alkyl.

The method for preparing high purity Group III metal alkyl generally involves a distillation step. Since it is difficult to remove impurities having boiling points close to that of the Group III metal alkyl, the distillation step becomes more complex. One effective method for the removal of impurities having boiling points close to that of the Group III metal alkyl is described, for example, in JP-B 5-35154 (or WO 85/04405). This method involves forming an adduct of a Group III metal alkyl with a Group V donor ligand in a solvent, removing along with the solvent impurities that do not form the adduct, and effecting thermal dissociation, thereby recovering the Group III metal alkyl.

Undesirably, this method uses benzene, pentane or hexane as the solvent, which must be removed. Although the solvent is allegedly removed by vacuum evaporation, a long time is necessary until the solvent is completely removed from the solid by vacuum evaporation, which is disadvantageous from the industrial aspect. If an amount of the solvent is left behind, the Group III metal alkyl after thermal dissociation contains a trace of the solvent, requiring the step of separating the solvent from the Group III metal alkyl.

In the manufacturing of trimethyl gallium, the boiling point of a solvent such as benzene, pentane or hexane is close to the boiling point of trimethyl gallium. A greater burden is then imposed on the step of removing the residual solvent.

In the manufacturing of triethyl gallium, trimethyl aluminum or the like, the boiling point of the solvent used is lower than the boiling point of the Group III metal alkyl. This means that upon removal of the residual solvent by distillation, the distillation of the solvent is followed by the distillation of the Group III metal alkyl. A careful operation must be taken so as to prevent the line from being contaminated.

A similar purification method is disclosed in JP-A 62-185090. This method involves forming a coordinate compound of an alkyl gallium with a Lewis base, separating an impurity component from the coordinate compound, subjecting the coordinate compound to dissociative distillation, thereby recovering the alkyl gallium. In this method, distillation or evaporation making use of a boiling point difference is carried out for the separation of the coordinate compound and the impurity component. For providing a separating gas for concomitantly carrying away the impurity component, a method of blowing an inert gas and the utilization of an un-coordinate alkyl gallium or a lower hydrocarbon are described.

However, the method of blowing an inert gas is difficult, when the coordinate compound is solid, to completely separate the impurity component from within the solid. The utilization of an un-coordinate alkyl gallium gives rise to a loss of alkyl gallium. In the event of lower hydrocarbon, it is difficult to separate the lower hydrocarbon if left behind.

The above-referred JP-A 62-185090 also describes recrystallization for the separation of the impurity component. Since the Group III metal alkyl must be handled in an inert gas-filled equipment, the workup of crystals as by washing becomes cumbersome in a scale-up system. If low hydrocarbon is used as a solvent, the separation of the solvent becomes difficult. It is thus difficult to implement the method of this patent in practice.

With these problems taken into account, a purification method of easily removing a solvent is strongly desired for the manufacturing of a Group III metal alkyl through thermal dissociation of an alkyl adduct.

SUMMARY OF THE INVENTION

In connection with a process of preparing a high purity Group III metal hydrocarbon through thermal dissociation of a Group III metal hydrocarbon adduct wherein a solvent may be introduced at any stage, an object of the invention is to provide a metal hydrocarbon purifying method capable of easily separating the solvent in a subsequent step.

It has been found that if a solvent having a boiling point which is up to 200° C., but at least 30° C. higher than the boiling point of a Group III metal hydrocarbon having the general formula (1) shown below is used in forming a Group III metal hydrocarbon adduct, typically a metal alkyl adduct, having the general formula (2) shown below, so that the solvent is co-present in the adduct, then the solvent can be readily removed from the Group III metal hydrocarbon adduct.

Accordingly, the present invention provides a method for purifying a Group III metal hydrocarbon having the general formula (1):

$$R^1R^2R^3M \qquad (1)$$

wherein $R^1$, $R^2$ and $R^3$ are each independently a monovalent hydrocarbon group of 1 to 6 carbon atoms, and M is a Group III metal element, the method comprising the steps of providing a Group III metal hydrocarbon adduct having the general formula (2):

$$(R^1R^2R^3M)_xL \quad (2)$$

wherein $R^1$, $R^2$, $R^3$, and M are as defined above, L is a Lewis base, and x is an integer equal to the number of donor atoms present in the Lewis base, in a solvent having a boiling point which is up to 200° C., but at least 30° C. higher than the boiling point of the Group III metal hydrocarbon having formula (1), preferably separating the solvent from the adduct, and causing the adduct to undergo thermal dissociation, thereby releasing the Group III metal hydrocarbon.

DESCRIPTION OF THE PREFERRED EMBODIMENT

The method of the invention employs a metal hydrocarbon adduct having the general formula (2).

$$(R^1R^2R^3M)_xL \quad (2)$$

Herein $R^1$, $R^2$ and $R^3$ are monovalent hydrocarbon groups of 1 to 6 carbon atoms, preferably 1 to 4 carbon atoms. These hydrocarbon groups may be either straight, branched or cyclic and either saturated or unsaturated. $R^1$, $R^2$ and $R^3$ may be the same or different. Preferably $R^1$, $R^2$ and $R^3$ are alkyl groups. Specific examples of $R^1$, $R^2$ and $R^3$ include methyl, ethyl, n-propyl, isopropyl, n-butyl, sec-butyl, tert-butyl, n-pentyl and cyclohexyl.

M is a Group III metal element, typically aluminum, gallium and indium.

L is a Lewis base such as amine compounds, phosphine compounds and ether compounds. The subscript x is an integer equal to the number of donor atoms present in the Lewis base. The Lewis base represented by L may be either solid or liquid at room temperature, but should have a higher boiling point than a Group III metal hydrocarbon having the general formula (1):

$$R^1R^2R^3M \quad (1)$$

wherein $R^1$, $R^2$, $R^3$, and M are as defined above. If a Lewis base has a lower boiling point, it can be entrained on the Group III metal hydrocarbon after thermal dissociation, resulting in the Group III metal hydrocarbon having a lower purity.

Referring to examples of the Lewis base, suitable amine compounds include tripentylamine, dioctylamine, N-methyloctadecylamine, trihexylamine, triphenylamine, trioctylamine, N,N-diethylaniline, N,N,N',N'-tetramethyl-1,4-phenylenediamine and N,N'-dimethyldodecylamine. Suitable phosphine compounds include tri-n-butylphosphine, tri-n-octylphosphine, tricyclohexylphosphine, triphenylphosphine, tribenzylphosphine, DIPHOS ($Ph_2PCH_2CH_2PPh_2$), and TRIPHOS ($Ph_2PCH_2CH_2P(Ph)CH_2CH_2PPh_2$) wherein Ph stands for phenyl. Suitable ether compounds include dihexyl ether, dioctyl ether, 2-methoxyethyl ether, and 2-ethoxyethyl ether. Inter alia, organophosphines, typically triphenylphosphine, are preferred because they possess almost nil vapor pressure so that they may be little entrained on the Group III metal hydrocarbon after thermal dissociation.

In forming a metal hydrocarbon adduct having formula (2): $(R^1R^2R^3M)_xL$, it is acceptable to employ a process of forming a metal hydrocarbon adduct from a Group III metal hydrocarbon and a Lewis base other than the above-specified Lewis base, and contacting the adduct with a Lewis base selected from among the above-specified amine compounds, phosphine compounds and ether compounds, thereby forming a metal hydrocarbon adduct having formula (2) through Lewis base exchange.

Preferably the metal hydrocarbon adduct is formed by contacting a Group III metal hydrocarbon with a Lewis base in the presence of a solvent having a boiling point which is up to 200° C., but at least 30° C. higher than the boiling point of the Group III metal hydrocarbon. In an alternative process, the metal hydrocarbon adduct is formed in the absence of any solvent or in the presence of another solvent, then mixed with a solvent having a boiling point which is up to 200° C., but at least 30° C. higher than the boiling point of the Group III metal hydrocarbon.

The solvent used is preferably selected from saturated or unsaturated aliphatic hydrocarbons, aromatic hydrocarbons and halogenated derivatives thereof although any solvent which is neither reactive nor decomposable with the Group III metal hydrocarbon may be used. In the event the Lewis base is solid, the use of an aromatic hydrocarbon solvent ensures ease of operation because the solubility of the Lewis base therein is high.

The boiling point of the solvent must be at least 30° C. higher than the boiling point of the Group III metal hydrocarbon for the reason that even if the solvent is carried on the Group III metal hydrocarbon as purified, they can be separated simply by distillation or evaporation making use of a vapor pressure difference therebetween. For example, when the Group III metal hydrocarbon is trimethyl gallium having a boiling point of 56° C., the solvent should have a boiling point of at least 86° C.; for trimethyl aluminum having a boiling point of 127° C., the solvent should have a boiling point of at least 157° C.; for trimethyl indium having a boiling point of 136° C., the solvent should have a boiling point of at least 166° C.; for triethyl gallium having a boiling point of 143° C., the solvent should have a boiling point of at least 173° C.

Illustrative examples of the solvent include n-heptane, n-octane, 2,2,3-trimethylpentane, 2,2,3-triethylpentane, n-nonane, 2,2,5-trimethylhexane, n-decane, toluene, o-xylene, m-xylene, p-xylene, ethylbenzene, cumene, mesitylene, n-butylbenzene, sec-butylbenzene, tert-butylbenzene, p-cymene, o-diethylbenzene, m-diethylbenzene, p-diethylbenzene, styrene, methylcyclohexane, ethylcyclohexane, p-menthane, α-pinene, dipentene, decalin, 1,1,2-trichloroethane, 1,1,1,2-tetrachloroethane, 1,1,2,2-tetrachloroethane, pentachloroethane, hexachloroethane, tetrachloroethylene, 1,2-dichloropropane, 1,2,3-trichloropropane, 1-chloropentane, chlorobenzene, o-dichlorobenzene, m-dichlorobenzene, p-dichlorobenzene, o-chlorotoluene, p-chlorotoluene, bromoform, 1,2-dibromoethane, 1,1,2,2-tetrabromoethane, bromobenzene, benzotrifluoride, and 1-bromo-2-chloroethane. Of these solvents, an appropriate solvent which can be used is selected in accordance with the boiling point of the Group III metal hydrocarbon.

Additionally, the solvent which can be used should have a boiling point of not higher than 200° C. If a solvent having a boiling point in excess of 200° C. is used, it has too low a vapor pressure to distill off when the metal hydrocarbon adduct and the solvent are separated by distillation or evaporation. Since impurities in the Group III metal hydrocarbon are removed by utilizing the solvent as a carrier gas at the same time when the solvent is distilled off, the use of the solvent having a boiling point in excess of 200° C. undesirably makes the removal of impurities inefficient.

Preferably the solvent is removed prior to the thermal dissociation of the metal hydrocarbon adduct. In the event that the boiling points of the Group III metal hydrocarbon and the solvent differ largely, the removal of the solvent need not be complete because the solvent can be separated simply by distillation or evaporation after the thermal dissociation into the Group III metal hydrocarbon. The solvent separation is generally effected by distillation or evaporation at reduced pressure and elevated temperature although the solvent can be separated by other commercially acceptable methods.

The solvent used may be a single solvent or a mixture of any. In the case of a solvent mixture, as long as one component has a boiling point of at least 30° C. higher than that of the Group III metal hydrocarbon, the other component(s) may not have a boiling point of at least 30° C. higher than that of the Group III metal hydrocarbon. The reason is that when the solvent is separated from the metal hydrocarbon adduct by heating under reduced pressure, the low-boiling solvent component is first removed, and the high-boiling solvent component is subsequently removed, with no low-boiling solvent component being left behind.

The solvent mixture, when used, may contain a solvent component having a boiling point in excess of 200° C. This does not affect the efficiency of impurity removal because impurities in the Group III metal hydrocarbon are removed together with the low-boiling solvent component. Even if the solvent component having a boiling point in excess of 200° C. is concomitantly carried on the Group III metal hydrocarbon after thermal dissociation, that component can be readily separated by making use of a boiling point difference.

It is preferred for efficient removal of impurities and efficient separation of the solvent that a proportion of the solvent having a boiling point which is up to 200° C., but at least 30° C. higher than the boiling point of the Group III metal hydrocarbon be at least 50% by weight, more preferably at least 70% by weight of the solvent mixture.

Thermal dissociation of the metal hydrocarbon adduct is generally carried out by heating at or above the dissociation temperature under reduced pressure. The reduced pressure is unnecessary if dissociation takes place under ambient pressure. The upper limit of dissociation temperature is not critical. Usually the adduct is heated at a temperature below the decomposition temperature of Group III metal hydrocarbon because heating above the decomposition temperature can generate impurities.

The Group III metal hydrocarbon resulting from thermal dissociation is generally recovered in a vessel which is cooled to a temperature at which the Group III metal hydrocarbon has a fully low vapor pressure. By supplying an inert gas flow during the thermal dissociation, a more efficient recovery of the Group III metal hydrocarbon can be achieved.

The series of operation is preferably carried out in an inert atmosphere and usually under atmospheric pressure or subatmospheric pressure. As the case may be, even operation under applied pressure is acceptable.

According to the invention, since the solvent which can be concomitantly carried over upon purification of Group III metal hydrocarbon has a boiling point which is at least 30° C. higher than that of Group III metal hydrocarbon, the solvent can be readily separated from the Group III metal hydrocarbon. The Group III metal hydrocarbon of high purity is obtained through a simple process.

EXAMPLE

Example and Comparative Example are given below for illustrating the invention, but the invention is not limited thereto.

Example 1

In a helium atmosphere, 250 g of xylene was premixed with 350 g (1.33 mol) of triphenylphosphine. To the premix, 134 g (1.17 mol) of trimethyl gallium contaminated with 5,400 ppb of siliceous impurities was added to form a metal alkyl adduct.

The mixture was heated at 70° C. under a vacuum of 0.2 kPa whereby the xylene solvent was distilled off. The adduct was then heated at 200° C. under a vacuum of 0.2 kPa for thermal dissociation into trimethyl gallium. Trimethyl gallium as dissociated was collected in a dry ice-cooled vessel. The percent recovery was 95%.

NMR and GC mass analysis revealed that the trimethyl gallium recovered contained about 1% of xylene.

The trimethyl gallium recovered was fed into a distillation column of 12 mm inner diameter and 100 mm height packed with Heli Pack No. 2 (Tokyo Tokushu Kanaami K.K.). The distillate was recovered from the initial fraction to the last, with a recovery rate of 90%.

On NMR and GC mass analysis of trimethyl gallium as distilled, no xylene was detected. Even on ICP analysis, no siliceous compounds were found.

It was proven that trimethyl gallium was removed of impurities and the solvent used could be separated by simple operation.

Comparative Example 1

The same run as Example 1 was repeated except that the solvent used was benzene. On analysis of the distillate, no siliceous compounds were found, but about 10 ppm of benzene was found, indicating that the solvent could not be completely removed.

Japanese Patent Application No. 2003-174387 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for purifying a Group III metal hydrocarbon having the general formula (1):

$$R^1R^2R^3M \quad (1)$$

wherein $R^1$, $R^2$ and $R^3$ are each independently a monovalent hydrocarbon group of 1 to 6 carbon atoms, and M is a Group III metal element, said method comprising the steps of (a) providing a Group III metal hydrocarbon adduct having the general formula (2):

$$(R^1R^2R^3M)_xL \quad (2)$$

wherein $R^1$, $R^2$, $R^3$, and M are as defined above, L is a Lewis base, and x is an integer equal to the number of donor atoms present in the Lewis base, in a solvent having a boiling point which is up to 200° C., but at least 30° C. higher than the boiling point of the Group III metal hydrocarbon having formula (1), and (b) causing said adduct to undergo thermal dissociation, thereby releasing the Group III metal hydrocarbon.

2. The method of claim 1 wherein the Lewis acid represented by L is an organophosphine.

3. The method of claim 1 wherein said solvent is an aromatic hydrocarbon.

4. The method of claim 3 wherein said solvent is selected from the group consisting of toluene, xylene, mesitylene and mixtures thereof.

5. The method of claim 1 wherein the Group III metal hydrocarbon is trimethyl gallium.

6. The method of claim 1, further comprising the step of separating the solvent from the adduct by distillation or evaporation, prior to the thermal dissociation step (b).

7. The method of claim 1, further comprising the step of distilling or evaporating the purified metal hydrocarbon.

8. The method of claim 2 wherein the organophosphine is a triphenylphosphine.

* * * * *

UNITED STATES PATENT AND TRADEMARK OFFICE
CERTIFICATE OF CORRECTION

| | | |
|---|---|---|
| PATENT NO. | : 7,005,530 B2 | Page 1 of 1 |
| APPLICATION NO. | : 10/868980 | |
| DATED | : February 28, 2006 | |
| INVENTOR(S) | : Hiromi Nishiwaki et al. | |

It is certified that error appears in the above-identified patent and that said Letters Patent is hereby corrected as shown below:

In the Claims:

In Claim 2, column 8, line 1, "Lewis acid" should read --Lewis base --

Signed and Sealed this

Fifth Day of December, 2006

JON W. DUDAS
*Director of the United States Patent and Trademark Office*